United States Patent
White

(10) Patent No.: US 11,305,079 B2
(45) Date of Patent: Apr. 19, 2022

(54) OXYGEN ENHANCED EXERCISE AND REST SYSTEM

(71) Applicant: OPTIMAL BREATHING, LLC, Fort Mill, SC (US)

(72) Inventor: Michael Grant White, Charlotte, NC (US)

(73) Assignee: OPTIMAL BREATHING, LLC, Fort Mill, SC (US)

( * ) Notice: Subject to any disclaimer, the term of this patent is extended or adjusted under 35 U.S.C. 154(b) by 756 days.

(21) Appl. No.: 15/973,625

(22) Filed: May 8, 2018

(65) Prior Publication Data

US 2019/0344031 A1    Nov. 14, 2019

(51) Int. Cl.
| | |
|---|---|
| *A62B 18/02* | (2006.01) |
| *A61M 16/00* | (2006.01) |
| *A61M 16/06* | (2006.01) |
| *A61M 16/10* | (2006.01) |
| *A61M 16/08* | (2006.01) |

(52) U.S. Cl.
CPC .... *A61M 16/0078* (2013.01); *A61M 16/0045* (2013.01); *A61M 16/06* (2013.01); *A61M 16/0816* (2013.01); *A61M 16/0883* (2014.02); *A61M 16/101* (2014.02); *A61M 2205/056* (2013.01); *A61M 2205/6036* (2013.01)

(58) Field of Classification Search
CPC .................................................. A61M 16/0078
See application file for complete search history.

(56) References Cited

U.S. PATENT DOCUMENTS

| | | | | | |
|---|---|---|---|---|---|
| 3,073,302 | A | * | 1/1963 | Bloom .................... | A62B 18/08 128/201.19 |
| 3,088,456 | A | * | 5/1963 | Stanton ............. | A61M 16/0081 128/204.25 |
| 4,440,163 | A | * | 4/1984 | Spergel .................. | A62B 18/04 128/205.13 |
| 4,840,170 | A | * | 6/1989 | Dahrendorf .............. | A62B 9/00 128/202.26 |
| 4,960,121 | A | * | 10/1990 | Nelson ................. | A62B 18/025 128/206.24 |
| 5,269,293 | A | * | 12/1993 | Loser ...................... | F25B 17/08 128/204.15 |
| 5,522,749 | A | * | 6/1996 | McNaughton ............ | B63C 9/08 2/6.1 |

(Continued)

*Primary Examiner* — Bradley H Philips
(74) *Attorney, Agent, or Firm* — Clements Bernard Baratta; Jacob P. Beers

(57) ABSTRACT

The present invention provides methods and systems for a breathing system, comprising breathing apparatus having a rigid base structure having a top portion, a bottom portion, an internal surface, and an external surface, wherein the top portion contains an arcuate section for covering a user's nose and the bottom portion is wider than the top portion for covering a user's mouth, the base structure contains an outer edge. A facepiece is engaged to the outer edge of the base structure and surrounds the base structure. A side passageway is disposed on a side of the base structure and is surrounded by a rim on the external surface of the base structure that extends outwardly from the external surface. A hose attachment device is selectively secured to the rim. The system also includes a storage device, and an oxygen supply.

11 Claims, 8 Drawing Sheets

(56) References Cited

U.S. PATENT DOCUMENTS

| | | | | |
|---|---|---|---|---|
| 6,352,077 B1* | 3/2002 | Shah | ............... | A61M 16/08 |
| | | | | 128/205.17 |
| 7,207,328 B1* | 4/2007 | Altemus | ........... | A61M 16/0078 |
| | | | | 128/202.28 |
| 2003/0047183 A1* | 3/2003 | Kiefer | ............... | A62B 18/08 |
| | | | | 128/201.15 |
| 2005/0199240 A1* | 9/2005 | Hall | ............... | A61M 16/0825 |
| | | | | 128/206.26 |
| 2006/0005831 A1* | 1/2006 | Stewart | ............... | B63C 9/1255 |
| | | | | 128/201.27 |
| 2008/0178886 A1* | 7/2008 | Lieberman | ........... | A61M 16/06 |
| | | | | 128/206.24 |
| 2009/0095301 A1* | 4/2009 | Hitchcock | ........... | A61M 16/06 |
| | | | | 128/206.21 |
| 2012/0048275 A1* | 3/2012 | Cowgill | ............ | A62B 7/08 |
| | | | | 128/205.28 |
| 2012/0216806 A1* | 8/2012 | Rookard | ............ | A61M 16/06 |
| | | | | 128/203.29 |
| 2014/0230821 A1* | 8/2014 | Warters | ............ | A61M 16/0622 |
| | | | | 128/205.25 |
| 2014/0261406 A1* | 9/2014 | Fabian | ............... | A62B 7/14 |
| | | | | 128/202.14 |
| 2015/0128944 A1* | 5/2015 | Buechi | ............ | A61M 16/0003 |
| | | | | 128/203.27 |
| 2018/0021605 A1* | 1/2018 | Bartkoski | ........... | A62B 18/006 |
| | | | | 128/205.12 |
| 2018/0361092 A1* | 12/2018 | Crowell | ............ | A62B 7/00 |

* cited by examiner

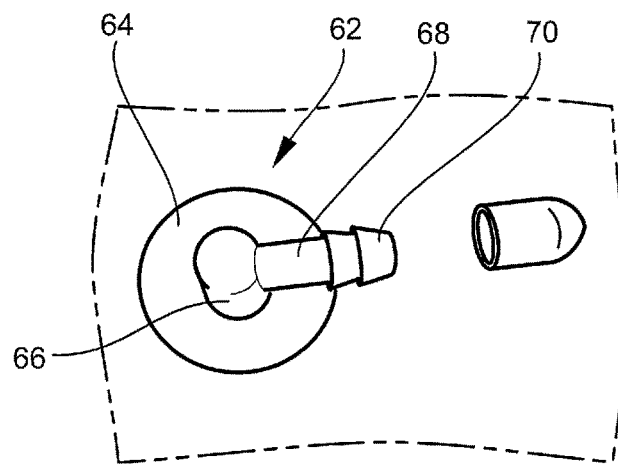
FIG. 8
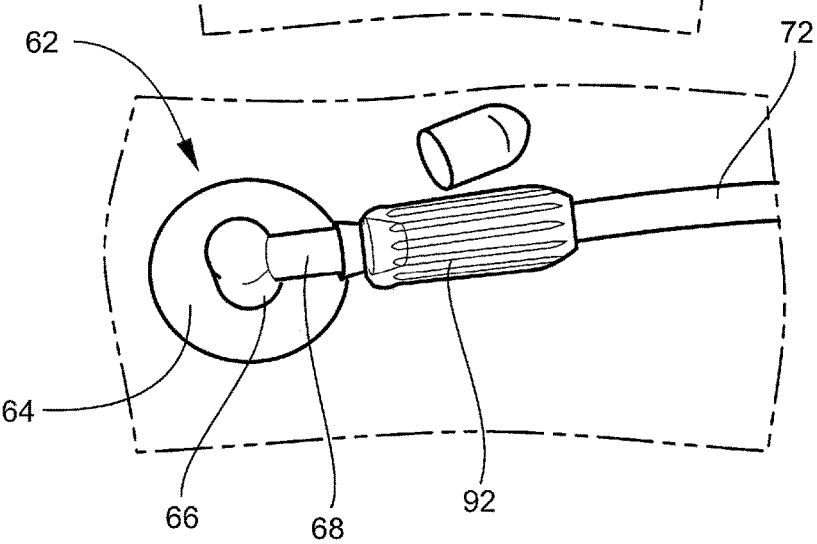
FIG. 9
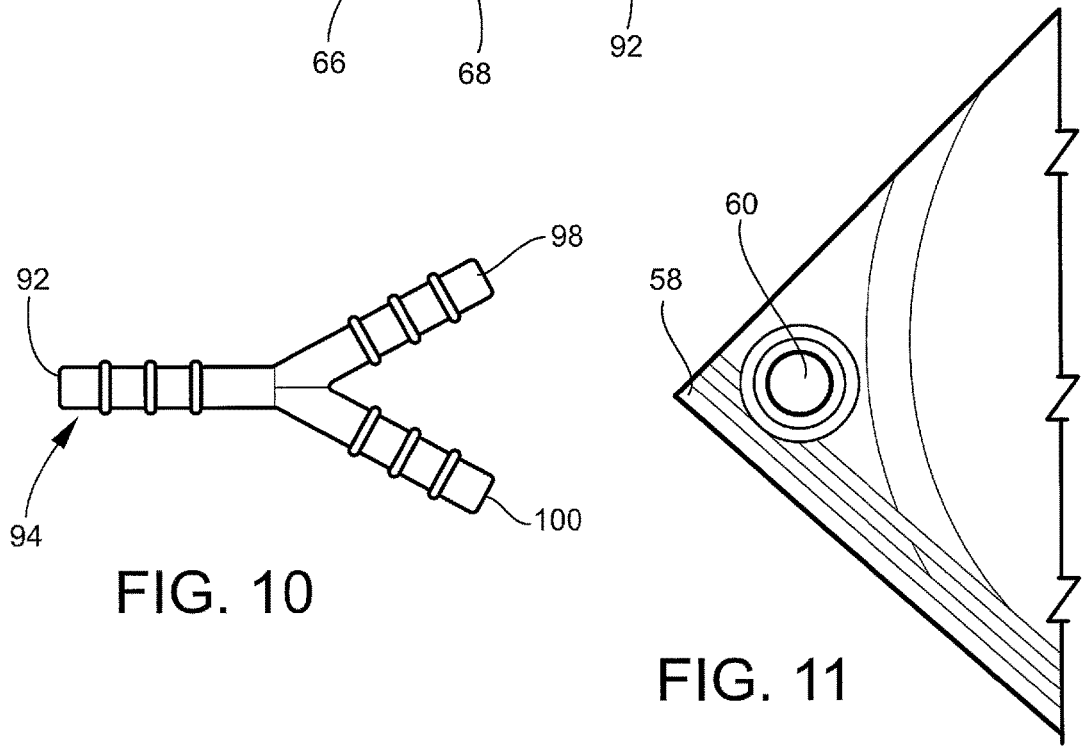
FIG. 10
FIG. 11

OXYGEN ENHANCED EXERCISE AND REST SYSTEM

FIELD OF THE INVENTION

The present invention relates generally to a breathing system and more generally relates to an oxygen enhanced exercise and rest system comprising a breathing apparatus coupled to an oxygen storage device.

BACKGROUND OF THE INVENTION

Breathing and oxygen intake are not only required for our survival, but breathing supplemental oxygen, especially accomplished under controlled conditions is good for our health and well being. Adding the oxygen to exercise adds valuable oxygen supplementation for natural cellular function. This can also allow breathing to be deeper and easier thus avoiding body tension-causing gasping and breath heaving during exercise or rest inviting harmful hyperventilation, reduced stress and anxiety. Hyperventilation can cause body tension, breathing restriction, poor gas exchange, and compromised cellular function resulting in respiratory problems and related oxygen deficiency including heart conditions, strokes, depressions, asthma, high blood pressure and many other issues. It is an object of the present invention to provide a system that is a natural energy booster, allowing the individual to train, exercise or rest with maximum breathing ease, and/or at peak strength levels for accelerated conditioning and movement. Though there are no guarantees, past experience has shown that the benefits to health and well being can be quite profound.

BRIEF SUMMARY OF THE INVENTION

According to an embodiment of the present invention, the present invention provides methods and systems for a breathing system, comprising breathing apparatus having a rigid base structure having a top portion, a bottom portion, an internal surface, and an external surface, wherein the top portion contains an arcuate section for covering a user's nose and the bottom portion is wider than the top portion for covering a user's mouth, the base structure contains an outer edge. A facepiece is engaged to the outer edge of the base structure and surrounds the base structure. A side passageway is disposed on a side of the base structure and is surrounded by a rim on the external surface of the base structure that extends outwardly from the external surface. A hose attachment device is selectively secured to the rim. The system also includes a storage device, and an oxygen supply.

According to another embodiment of the present invention, the breathing apparatus contains a first end and a second end, the first end is engaged to the base structure and the second end contains an upper edge and an opening, the rim has an internal surface which allows oxygen to flow and an external surface containing at least one key near the upper edge.

According to yet another embodiment of the present invention, the breathing apparatus contains a first end and a second end, the first end is engaged to the base structure and the second end contains an upper edge and an opening, the rim has an internal surface which allows oxygen to flow and an external surface contains a plurality of keys near the upper edge and spaced an equal distance apart.

According to yet another embodiment of the present invention, the breathing apparatus contains a hose attachment device with a first end and a second end, wherein the first end contains a first concentric ring and a hollow tube extending outward from the concentric ring.

According to yet another embodiment of the present invention, the breathing apparatus contains a hose attachment device that has a first end and a second end, wherein the first end contains a first concentric ring and a second concentric ring engaged to a first side of the first concentric ring and a hollow tube extending outward from the second side of the first concentric ring.

According to yet another embodiment of the present invention, the breathing apparatus contains a rim and hose attachment device that are hollow.

According to yet another embodiment of the present invention, the breathing apparatus contains a second concentric ring that contains a lip positioned on the internal surface and contains at least one keyed opening for receiving a corresponding key positioned on the rim.

According to yet another embodiment of the present invention, the breathing apparatus includes a second concentric ring that contains a lip positioned on the internal surface and containing a plurality of keyed openings for receiving corresponding keys position on the rim.

According to yet another embodiment of the present invention, the breathing apparatus includes at least one front passageway disposed on the breathing apparatus.

According to yet another embodiment of the present invention, the breathing apparatus includes a front passageway that contains a hollow tube with an internal surface and an external surface, the front passageway extends outward from the front passageway and contains a bend at some distance from the base structure, the hollow tube extends to an outlet portion, the inner surface of the passageway allows oxygen to flow therethrough.

According to yet another embodiment of the present invention, the breathing apparatus includes an outlet portion that contains ridges on the external surface.

According to yet another embodiment of the present invention, the breathing apparatus according to Claim 9, wherein a plurality of front passageways are disposed on the breathing apparatus.

According to yet another embodiment of the present invention, a storage device includes a first side having an outer edge, a second side having an outer edge and the outer edge of the first side and the outer edge of the second side are engaged together forming an interior cavity. An inlet opening within either the first side or the second side for allowing oxygen to be inserted into the cavity, and a plurality of outlet openings within the first side and/or second side for allowing oxygen to exit the storage device.

According to yet another embodiment of the present invention, the storage device includes a first side that has two pairs of opposed edges and the second side has two pairs of opposed edges, the pairs of opposed edges of the first side and the second side are engaged to each other forming an interior cavity, the intersection of the sides forms a corner, resulting in the storage device containing four corners.

According to yet another embodiment of the present invention, the storage device includes a grommet is positioned in at least two corners of the storage device.

According to yet another embodiment of the present invention, the breathing system includes a breathing apparatus that has a rigid base structure having a top portion, a bottom portion, an internal surface, and an external surface, wherein the top portion contains an arcuate section for covering a user's nose and the bottom portion is wider than the top portion for covering a user's mouth and the base structure contains an outer edge. A facepiece is engaged to the outer edge of the base structure and surrounds the base structure. A side passageway is disposed on a side of the base structure and is surrounded by a rim on the external surface of the base structure that extends outwardly from the external surface, and a hose attachment device is selectively secured to the rim. The system includes a storage device and an oxygen supply.

According to yet another embodiment of the present invention, the storage device includes a first side having an outer edge, a second side having an outer edge and the outer edge of the first side and the outer edge of the second side are engaged together forming an interior cavity. An inlet opening within either the first side or the second side for allowing oxygen to be inserted into the cavity, and a plurality of outlet openings within the first side and/or second side for allowing oxygen to exit the storage device.

According to yet another embodiment of the present invention, the breathing system includes a hose having a first end and a second end, wherein the first end is engaged to a first adaptor and the second end is engaged to a second adaptor, the first adaptor is engaged to the rim of the breathing apparatus and the second adaptor is engaged to an outlet in the storage device.

According to yet another embodiment of the present invention, the breathing system includes a hose having a first end and a second end, the first end of the hose engaged to the oxygen supply and the second end engaged to the inlet opening in the storage device.

According to yet another embodiment of the present invention, the breathing system includes a storage device composed of medical grade thermoplastic polyurethane.

BRIEF DESCRIPTION OF THE DRAWINGS

The present invention is illustrated and described herein with reference to the various drawings, in which like reference numbers denote like method steps and/or system components, respectively, and in which:

FIG. 8 is a top perspective view of the nipple structure of the storage device of the present invention;

FIG. 9 is a top perspective view of the nipple structure of the storage device of the present invention with an adaptor and hose attached;

FIG. 10 is a top view of a splitter that may be used with the present invention;

FIG. 11 is a top view of a corner of the storage device containing a grommet;

DETAILED DESCRIPTION OF THE INVENTION

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
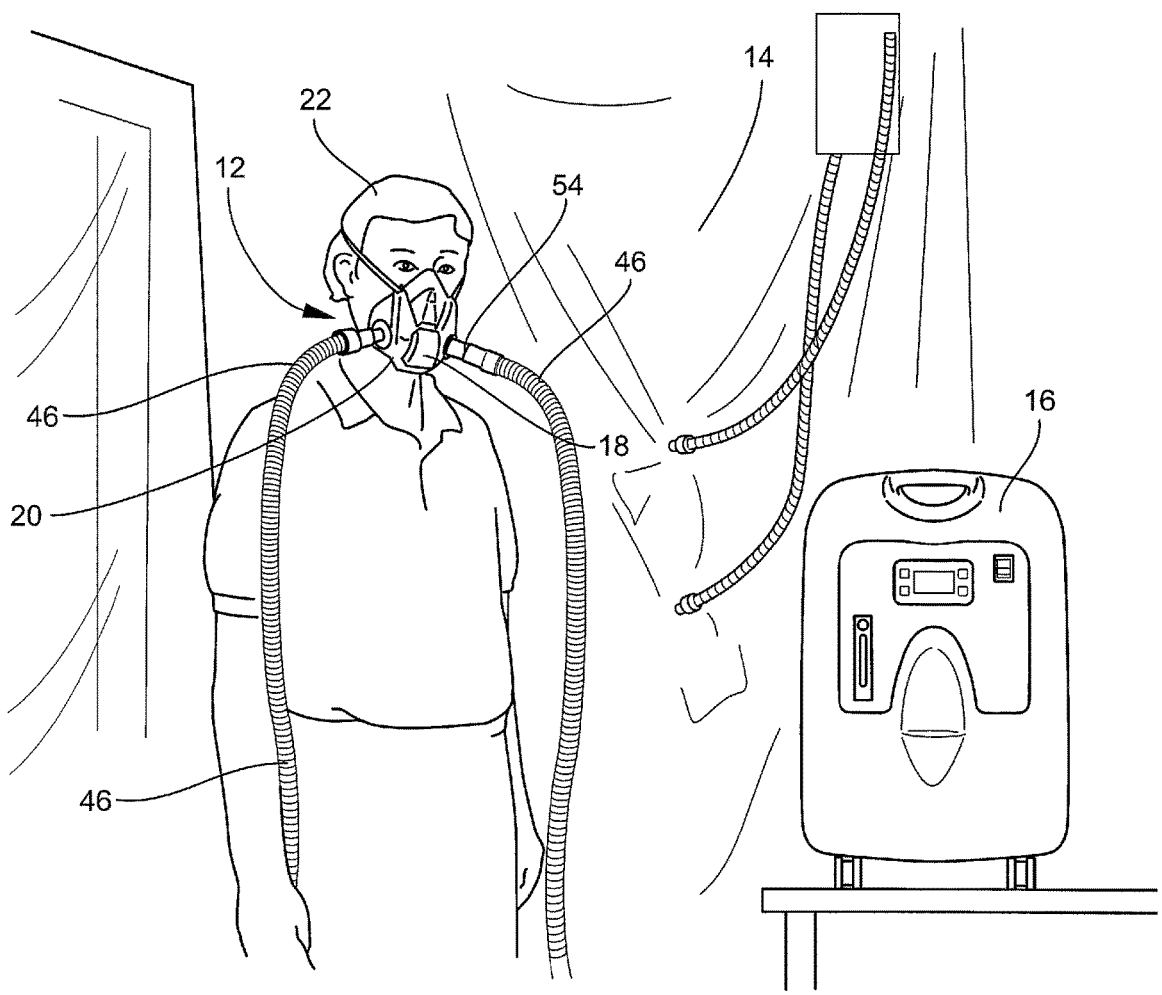
FIG. 1 is a perspective view of a user using the present invention.
Figure 2:
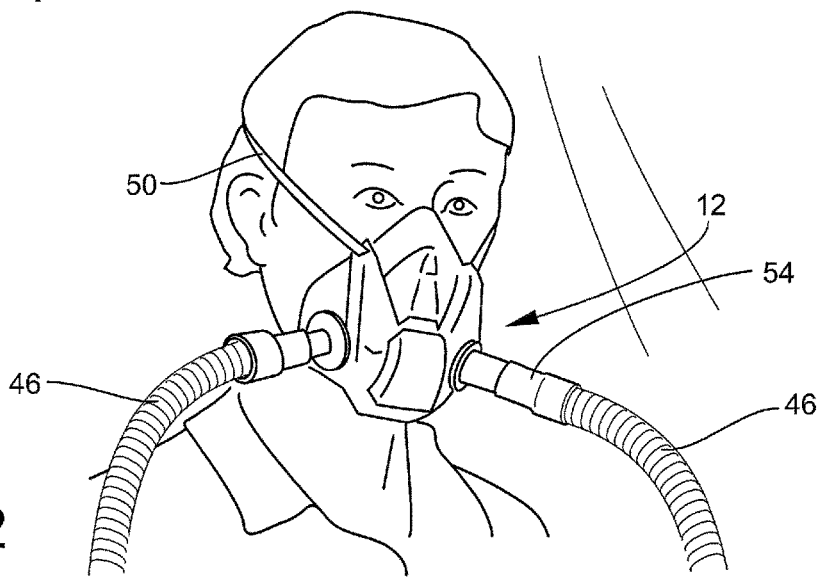
FIG. 2 is a perspective view of a user using the breathing apparatus.
Figure 7:
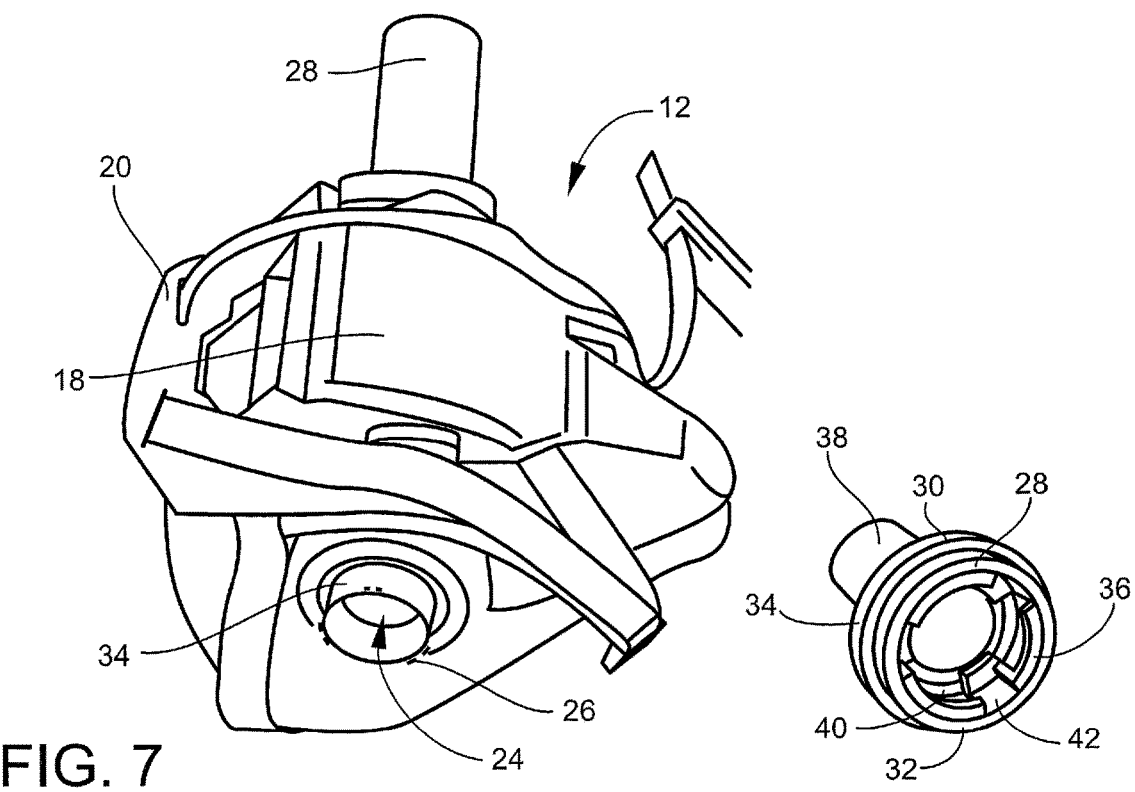
FIG. 7 is a side perspective view of the breathing apparatus of the present invention with a hose attachment device removed.

Referring now specifically to the drawings, an oxygen enhanced exercise and rest system is illustrated in FIG. 1 and is shown generally at reference numeral 10. The system 10 includes a breathing apparatus 12, an oxygen storage device 14, and an external oxygen supply device 16. The breathing apparatus 12 contains a rigid base structure 18 and an elastomeric facepiece 20 that extends from the base structure 18. The base structure 18 is illustrated in FIGS. 1, 2, and 7, wherein the base structure 18 is designed to cover the nose and mouth of a user 22. The base structure 18 includes an interior surface and an exterior surface. The base surface 18 is generally triangularly shaped and is generally convex. The top portion of the base structure 18 contains an arcuate section designed to be placed adjacent and over top the nose of a user 22. The bottom portion is designed to be placed adjacent and over top the mouth of a user 22. The bottom portion is wider than the top portion. An exhaust outlet is formed within the bottom portion of the base structure 18 for allowing air to flow out of the base structure 18, allowing the user 22 to exhale. A one-way valve is disposed adjacent the exhaust outlet allowing the user 22 to exhaust air out of the base structure 18 with allowing little or no air to enter the base structure 18 from this exhaust outlet. The external surface of the base structure 18 contains a cavity within the bottom portion. The exhausted air of the user 22 travels through the exhaust outlet and into the cavity and then through the cavity and external the breathing apparatus 12 and into the air surrounding the base structure 18. An external edge surrounds the entire base structure 18.

The facepiece 20 is engaged to the edge of the base structure 18 and extends outwardly from the facepiece 20. As the facepiece 20 extends outwardly, it curves in on itself at a distance from the base structure 18 forming an opening between the internal surfaces of the facepiece 20. When the facepiece 20 curves in on itself a contact surface is formed that contacts the user's 22 face. The facepiece 20 is much softer and comfortable for touching the skin of a user 22 than the base structure 20. The facepiece is also malleable, allowing the facepiece 20 to properly fit on almost all user's face.

Two side passageways 24 are disposed on either side of the base structure 18. The side passageways 24 are surrounded by a concentric rim 26 that surrounds the side passageways 24 on either side of the base structure 18. The concentric rim has a first end and a second end, wherein the first end is engaged to the external surface of the breathing apparatus 12, and more preferably the base structure 18. A filter may be placed within the side passageway 24 and rim 26 to filter the oxygen entering the internal side of the breathing apparatus 12. A hose attachment device 28 is engaged to and selectively secured to the rim 26. The first end of the hose attachment device 28, as shown in FIGS. 7, 12, 13, and 14, has a diameter larger than the diameter of the second end of the rim 26.

The first end of the hose attachment device 28 contains a first concentric ring 30 having a first side and a second side, a second concentric ring 32 is engaged to the first side of the first concentric ring 30 and the second concentric ring 32 has a diameter less than the diameter of the first concentric ring 30. A skirt 34 is formed at the intersection of the first concentric ring 30 and the second concentric ring 32. The internal side of the second concentric ring 32 contains a lip 36 formed therein and adjacent the opening of the second concentric ring 32.

A cylindrical, hollow tube 38 extends from the second side of the first concentric ring 30 and towards the second end of the hose attachment device 28. A shelf 40 is disposed on the internal side of the hose attachment device 28 at the juncture of the first concentric ring 30 and the hollow tube 38, which is the internal side of the skirt 34 formed on the exterior side of the hose attachment device 28.

The rim 26 contains at least one key 26 disposed on the external side of the rim 26 and near an upper edge of the rim 26 on the second end. The rim 26 may contain two or more keys 26 or a plurality of keys 26. The keys 26 are designed to receive a corresponding keyed opening 42 disposed on the lip 36 of the hose attachment device 28. The keyed opening 42 is placed above the key 26, wherein the hose attachment device 28 is placed over and onto the rim 34, in a telescopic relationship with each other, resulting in the key 26 sliding into the keyed opening 42 and contacting a ridge 44 disposed on the shelf 40. The lip 36 contains two or more keyed openings 42 or a plurality of keyed openings 42. Once the key 26 contacts the ridge 44, the hose attachment device 28 fully encompasses the rim 26 and may be rotated in the clockwise direction. The lip 36 is angled upwards along its initial length adjacent the keyed opening 42, and as the hose attachment device 28 is rotated, the bottom surface of the key 26 engages the lip 36 and moves along a distance of the lip 36. Initially, the bottom surface of the key 26 engages and then moves along the angled portion of the lip 36. It is only the initial portion of the lip 36 that is angled. As the key 26 moves along the angled portion of the lip 36 the key 26 is prevented from moving further preventing the hose attachment device 28 from rotating, caused by the key being unable to move any further along the angled portion of the lip 36, resulting in the hose attachment device 28 and rim 34 selectively secured to each other by friction fit.

Figure 12:
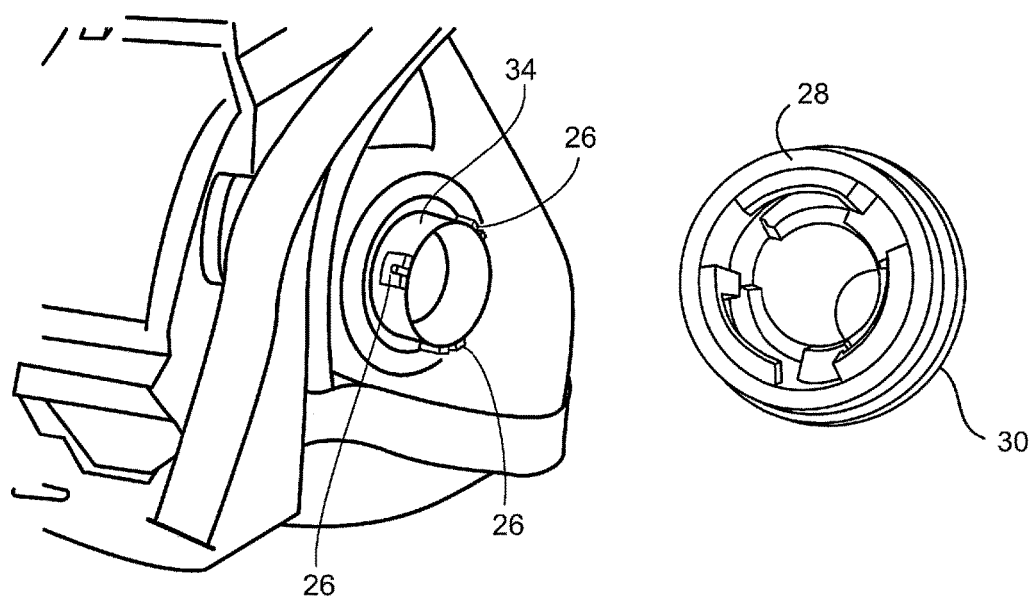
FIG. 12 a partial side view of the breathing apparatus and a bottom view of the hose attachment device.
Figure 13:
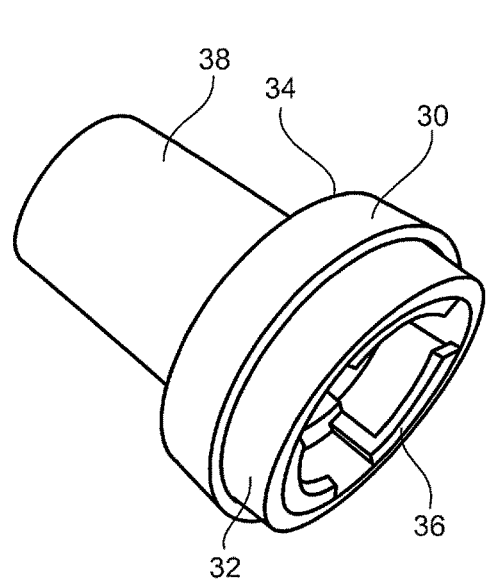
FIG. 13 is a side perspective view of the hose attachment device.
Figure 14:
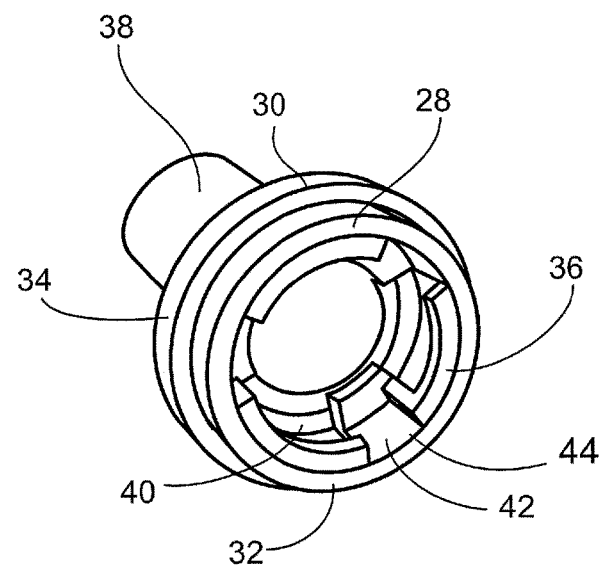
FIG. 14 is a bottom perspective view of the hose attachment device.

As illustrated in FIGS. 7 and 12, the rim 34 contains three keys 26. These keys 26 are disposed on the upper edge of the rim 34 and an equal distance apart. The keys 26 are generally square shaped and have a recess within the middle portion. The hose attachment device 28 contains a corresponding number of keyed openings 42. As shown in FIGS. 7, 12, and 14, the hose attachment device 28 contains three keyed openings 42 disposed within the lip 36 and spaced an equal distance apart that corresponds with the keys 26 positioned on the rim 34. The second end of the hose attachment device 28 is engaged to a flexible hose 46.

Figure 5:
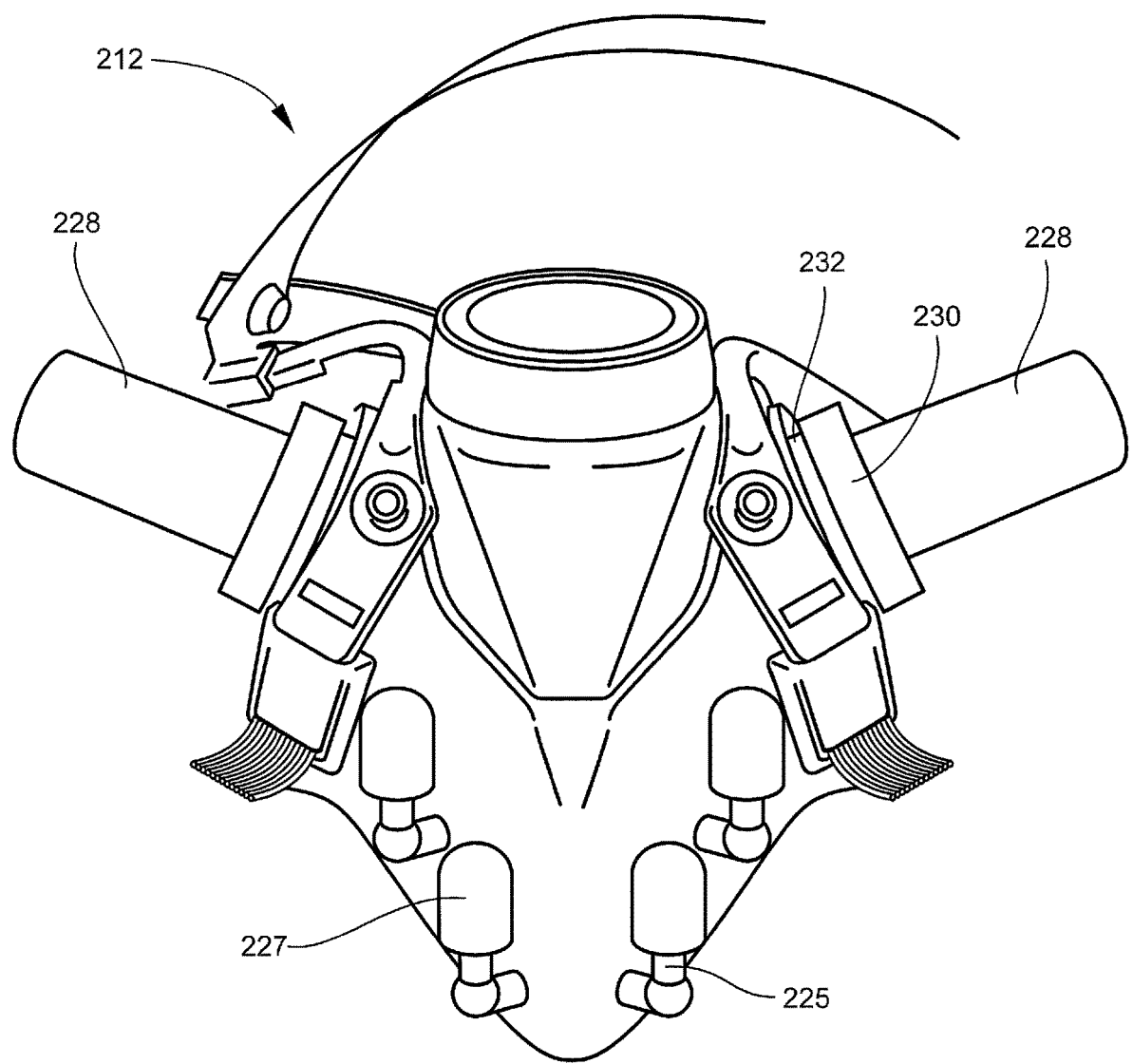
FIG. 5 is a top perspective view of an alternative embodiment of the breathing apparatus of the present invention.
Figure 6:
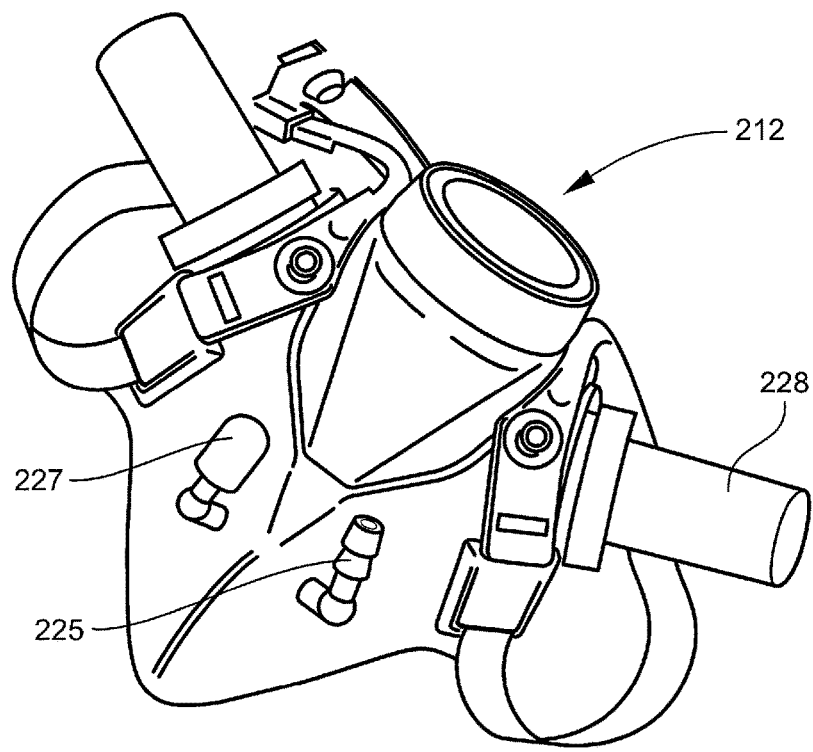
FIG. 6 is a top perspective view of the alternative embodiment of the breathing apparatus.

An alternative embodiment of the breathing apparatus 12 is illustrated in FIGS. 5 and 6. This breathing apparatus 212 contains a rigid base structure 218 and an elastomeric facepiece 220 that extends from the base structure 218. The base structure 218 is illustrated in FIGS. 1, 2, and 7, wherein the base structure 218 is designed to cover the nose and mouth of a user 22. The top portion of the base structure 218 contains an arcuate section designed to be placed adjacent and over top the nose of a user 22. The bottom portion is designed to be placed adjacent and over top the mouth of a user 22. An opening is formed within the bottom portion of the base structure 218 for allowing oxygen to flow within the base structure 218, allowing the user 22 to breath. The external side of the base structure 18 contains a generally circular structure that covers the opening. A one-way valve is disposed within the opening allowing the user 22 to exhaust air out of the base structure 218 with allowing little or no air to enter the base structure 218 from this opening. The exhausted air of the user 22 travels through the opening and into the circular structure and then through the cavity and into the air surrounding the base structure 218.

The facepiece 220 is engaged to the edges of the base structure 218 and extends outwardly from all edges of the facepiece 220. As the facepiece 220 extends outwardly, it curves in on itself at a distance from the base structure 218 forming an opening between the internal surfaces of the facepiece 220. When the facepiece 220 curves in on itself a contact surface is formed that contacts the user's 222 face. The facepiece 220 is much softer and comfortable for touching the skin of a user 22 than the base structure 220. The facepiece is also malleable, allowing the facepiece 220 to properly fit on almost all user's face.

Figure 15:
FIG. 15 illustrates a front passageway of located on an alternative embodiment of a breathing apparatus and its cover.

At least two side passageways 224 are disposed on the base structure 218. Two of the side passageways 224 are surrounding by a concentric rim 226 that surrounds the side passageways 224 on either side of the base structure 218. A filter may be placed within the side passageways 224 and rim 226 to filter the oxygen entering the internal side of the breathing apparatus 212. Front passageways 225 may be disposed on the elastomeric facepiece 220 and located in close proximity to the top portion of the base structure 218 and near the user's 22 nose. These front passageways 225, as illustrated in FIGS. 5, 6, and 15, consist of a hollow tube that extends outward from the facepiece 20. At a distance from the facepiece 20, the tube turns approximately 90° and extends to a ridged nipple portion. The ridge nipple portion contains two ridges for engaging a hose or the like. The ridges assist in retaining the hose over the nipple portion by friction fit. The four front passageways 225 are an optional feature and are meant to be custom fitted when applicable. A one foot smooth bore tube can be engaged to the ridge nipple portion of the front passageways 225 to capture exhaled air and rebreath $CO_2$. When the air openings are not in use, a cover 227 may be placed over the nipple portion. As illustrated in FIG. 5, four front passageways 225 may be positioned on the facepiece 20 and spaced an equal distance apart. It may be appropriate for those with poor enough lung function to need less $O_2$ and more $CO_2$, and therefore the four passageways 225 are designed for rebreathing $CO_2$. As mentioned above, the passageways 225 are options, but may be relevant in a possible future rebreathing application when the full load of O2 is utilized.

A head harness 48 is engaged to the breathing apparatus 12 by a pair of straps 50. The head harness 49 is generally oval shaped to be placed on the back of a user's 22 head. The head harness 48 is adjustable allowing the head harness 48 to securely fit on the head of a number of user's 22 with different sized heads. The head harness 48 has a first end and a second end. When the first end and the second end are joined together, the head harness 48 achieves its oval shape. The first end of the head harness 48 contains a plurality of holes. The second end of the head harness 48 contains a plurality of protrusions that are received within the holes. The holes of the head harness 48 are inserted into the different holes, allowing the diameter of the head harness 48 to increase and decrease depending upon the adjustment of the holes. Nylon or cloth straps 50 extend from the base structure 18 to the head harness 48. The straps 50 are adjustable, again allowing multiple users with different face sizes to use the breathing apparatus 12. Neck straps 52 may also be disposed on the bottom portion of the base structure 18. A first neck strap 52 extends outwards from one side of the base structure 18 and a second neck strap 52 extends outwards from the second side of the base structure 18. The first end of each neck strap 52 is engaged to the base structure 18 and the second ends are designed to be selectively secured to each other with a retention mechanism.

A flexible hose 46 is engaged to the second end of the hose attachment device 28. As illustrated, two flexible hoses 46, such as a CPAP hose or nylon hose, are engaged to each hose attachment device 28. The flexible hose 46 is engaged by the use of an adaptor 54. The adaptor 54 is a generally circular structure that is rigid. The adaptor 54 has a diameter that is slightly larger than the diameter of the hose attachment device 28 and engaged to each other by friction fit. The first end of the adaptor 54 is engaged to the second end of the hose attachment device 28. The flexible hose 46 is engaged to the second end of the adaptor 54. The flexible hose 46 has a first end and a second end. The first end is engaged to the adaptor 54 with the second end engaged to a machine or device that allows oxygen to flow through the flexible hose 46. The inside dimension of the flexible hose 46 is 17 mmID. In an alternative embodiment and a new way to augment $CO_2$, one of the flexible hoses 46 may be disconnected from the hose attachment device 28 and a two, six, or ten foot 17 mmID flexible hose 46, such as a CPAP hose or nylon hose, may be engaged to the hose attachment device 28 instead. In this embodiment, a first end of the CPAP hose is engaged to the hose attachment device 28 and the second end is not engaged to anything. In this embodiment, as the user 22 exhales, the $CO_2$ is partially recaptured in the CPAP hose and is rebreathed along with the $O_2$ from the flexible hose 46.

Figure 3:
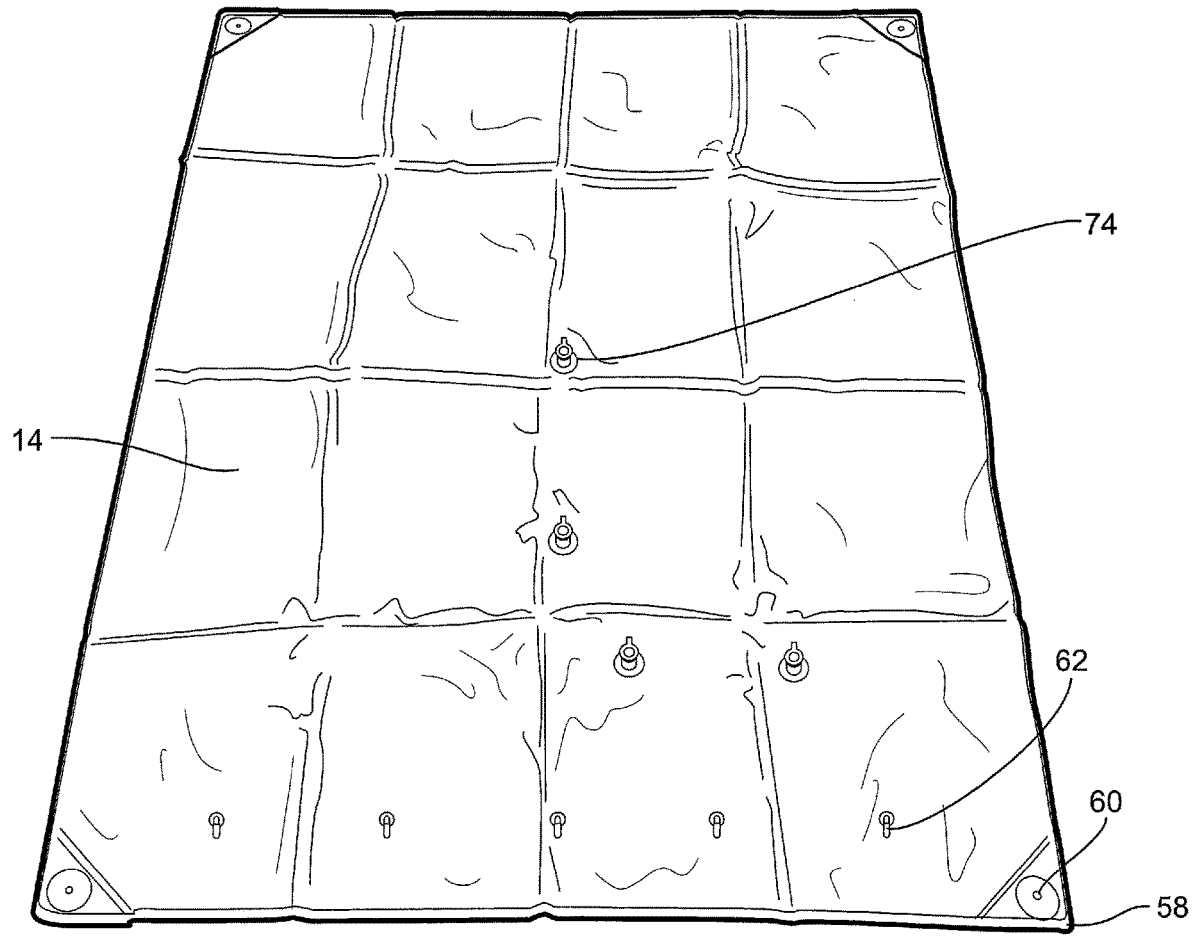
FIG. 3 is a perspective view of the storage device.
Figure 4:
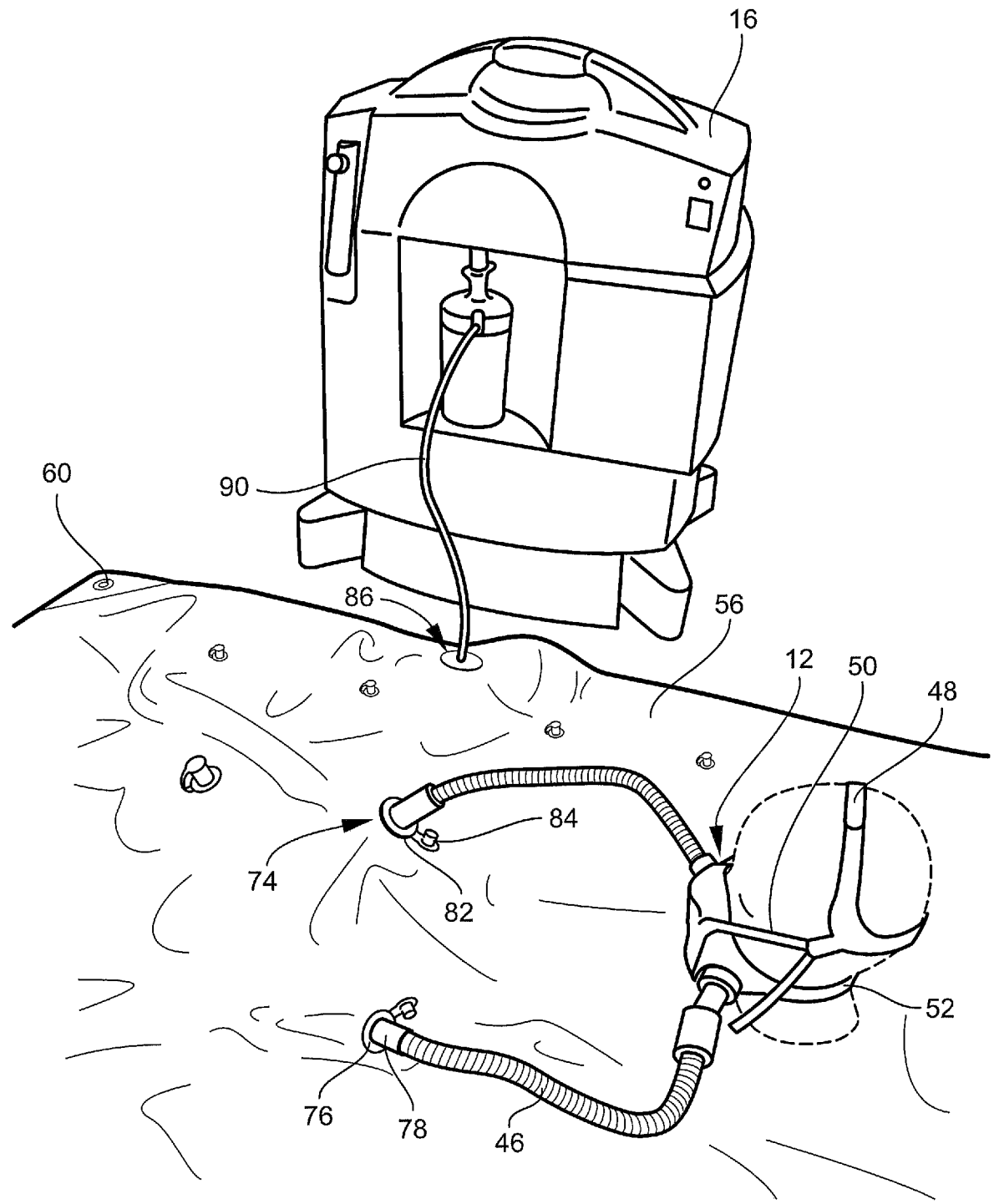
FIG. 4 is a perspective view of the present invention.

An oxygen storage device 14 is illustrated in FIGS. 3 and 4. The oxygen storage device 14 is preferably composed of a medical grade thermoplastic polyurethane (TPU). The storage device 14 contains a first side that extends to an outer edge and a second side that extends to an outer edge, wherein the outer edges of the first side and the outer edges of the second side are engaged to each other. As illustrated, the first side and the second side extend to four sides having an outer edge, wherein each outer edge of the first side and each outer edge of the second side are engaged to each other. The intersection of the sides form corners 58, as illustrated in FIG. 11. The corners may contain a generally circular grommet 60 for allowing the storage device to be hung from a ceiling or like structure as shown in FIG. 1.

The storage device 14 contains a plurality of holes contained on the first side, the second side, and/or both the first side and the second side. As illustrated in FIGS. 8 and 9, the holes are covered by a nipple structure 62. The nipple structure 62 contains a generally circular base 64 that contains a first portion engaged to the exterior surface of the side and around the hole and a second portion engaged to the interior surface of the side and around the hole. The circular base 64 provides structure to the outer surrounding of the hole and prevents the exterior of the hole from tearing or ripping. The base 64 is engaged to an upwardly extending hollow portion 66 that contains an opening at its upper end. An outwardly extending, hollow elongate piece 68 extends outwardly from the hollow piece 66 and engaged to the opening for allowing oxygen to flow between the hollow portion 66 to the elongate piece 68. The end of the elongate piece 68 contains raised ridges 70 for selectively securing a hose 72 for transporting the oxygen in the storage device 14 to an air opening 225 on the breathing apparatus 212.

A second set of openings 74 are disposed on the first side, the second side, and/or the first side and the second side of the oxygen storage device 14. As shown in FIG. 4, the openings contain a circular base 76 with a first portion engaged around the opening 74 on exterior side and a second portion engaged around the opening 74 on the interior side. The base 76 provides structure to the outer surrounding of the hole and preventing the exterior of the hole from tearing or ripping. An upwardly extending cylindrical tube 78 is engaged to the base 76 and extends upwardly. The tube 78 has a first end and a second end, wherein the first end of the tube 78 is engaged to the base 76 and allows oxygen to flow from the interior side of the storage device 14 to the second side of the tube 78.

A second adaptor 80 is engaged to the second end of the flexible hose 46. The flexible hose 46 is engaged to the first end of the second adaptor 80 and the second end is engaged to the tube 78. The second adaptor 80 has a diameter slightly larger than the diameter of the tube 78 allowing the second end of the adaptor to slide over the tube 78 forming a selectively secured arrangement, allowing oxygen to flow from the interior of the storage device 14 and through the hose 46. The base 76 may also contain an elongate flexible finger 82 extending therefrom that contains a cap 84 on one end. The cap 84 may be placed over the opening in the tube 78 for preventing oxygen from escaping when not in use.

As shown in FIG. 4, an inlet hole 86 is disposed on the first side of the storage device 14. Alternatively, an inlet hole 86 may be disposed on the second side or the first side and the second side. The inlet hole 86 allows oxygen to be pumped into the storage device 14. As shown in FIGS. 1 and 4, a regulated, external oxygen supply 16 may be used to pump oxygen into the storage device 14. An acceptable oxygen supply may be an Airsep® Newlife® Intensity Stationary Oxygen Concentrator from Caire® a Chart Industries Company. An inlet tube 90 extends from the oxygen supply 16 to the inlet hole 86, allowing oxygen to flow from the oxygen supply 16 to the interior of the storage device 14.

During use, oxygen is pumped from the oxygen supply and through the inlet tube that is inserted into the inlet hole 86. Through the inlet hole 86, oxygen enters the interior of the storage device 14. As the oxygen enters the interior of the storage device 14, the volume of the oxygen within the storage device 14 increases, expanding the storage device 14.

The breathing apparatus 12 is engaged to the storage device 14. As shown in FIGS. 1 and 4, the hose 46 is engaged to the breathing apparatus 12 and the storage device 14. More specifically, the first end of the hose 46 is engaged to a first adaptor 54 that is engaged to the hose attachment device 28. The second end of the hose is engaged to a second adaptor 80 that is engaged to storage device 14. More specifically, the opening within the storage device 14 contains a base 76 with a hollow portion and a hollow, cylindrical tube 78 extending therefrom, forming a continuous opening for allowing oxygen to flow through from the interior of the storage device 14, through the base, and out through the second end of the cylindrical tube 78. The oxygen flows through the hose 46, through the first adaptor 54, through the hose attachment device 28, and into the breathing apparatus 12. During use, the storage device 14 may be hung on a ceiling, wall, or other support structure with the use of the grommet 60 disposed on the corners 58 of the storage device 14. As the storage device 14, is hanging and oxygen is continuously pumped into the storage device 14, the user 22 is able to breathe oxygen through the breathing apparatus 12.

For additional oxygen, the breathing apparatus 212 may be utilized with at least one more opening for allowing oxygen into the breathing apparatus 212. A hose 72 is engaged to at least one air opening 225 disposed on the top portion of the breathing apparatus 212. The first side of the hose 72 is engaged to the air opening 225 and the second side is engaged to the nipple structure 62 on the storage device 14. The second side of the hose 72 is attached to the ridges 70 disposed on the exterior portion of the elongate piece 68 of the nipple structure 62. An adaptor 92, as shown in FIG. 9, may also be used for engaging the hose 72 to the nipple structure 62. The first end of the adaptor is engaged to the ridges 70 of the nipple structure 62 and the second end is engaged to the hose 72.

As shown in FIG. 5, four air openings 225 may be disposed on the breathing apparatus 212. As such four hoses 72 may be engaged to the air openings 225 in the breathing apparatus 212 that are also engaged to four nipple structures 62 of the storage device 14, allowing the breathing apparatus to have four air entryways in addition to the two side passageways 224 disposed on either side of the base structure 18 of the breathing apparatus 12.

Figure 16:
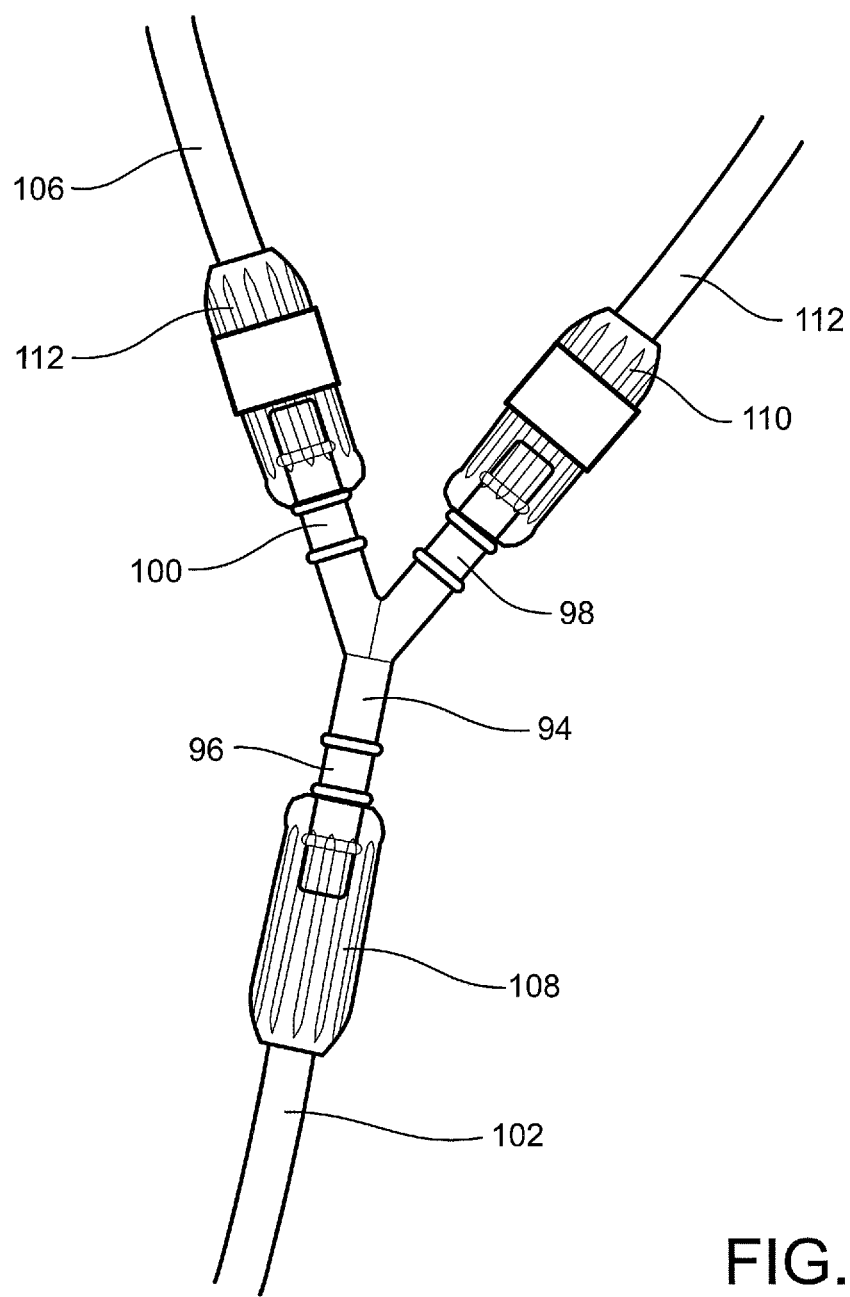
FIG. 16 illustrates a splitter with a first, second, and third adaptor engaged to a first, second, and third hose.

In another alternative embodiment, a splitter 94, as shown in FIG. 10, may be utilized within the invention and shown within FIG. 16. The splitter 94 receives oxygen within the opening 96 in the first portion allowing the oxygen to proceed down a hollow channel within the splitter 94. The splitter 94 splits, forming two hollow channels that diverge from the hollow channel on the first portion, forming a first outlet 98 and a second outlet 100 on the second portion. The exterior surface of the first portion contains raised, circular ridges that surround the exterior of the first portion. Likewise, raised, circular ridges surround the exterior of the second portion near the first outlet 98 and the second outlet 100. A first hose portion 102 extends from the storage device 14 to the opening 96 in the splitter 94. A second hose portion 104 extends from the first outlet 98 at a side passageway 24 on the breathing apparatus 12. A third hose portion 106 extends from the second outlet 100 to the other side passageway 24 of the breathing apparatus 12.

As illustrated, adaptors may be utilized to engaged the hose portions to the splitter 94. As illustrated in FIG. 16, a first adaptor 108 has a first end and a second end. The first end of the first adaptor 108 is engaged to the first hose 102 and the second end is engaged to the opening 96. The second adaptor 110 has a first end and a second end. The first end of the second adaptor 110 is engaged to the first outlet 98 and the second end is engaged to the first hose portion 106. The third adaptor 112 has a first end and a second end. The first end is engaged to the second outlet 100 and the second end is engaged to the third hose portion 106.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. A breathing apparatus, comprising:
   a rigid base structure having a top portion, a bottom portion, an internal surface, and an external surface, wherein the top portion contains an arcuate section for covering a user's nose and the bottom portion is wider than the top portion for covering a user's mouth, the base structure contains an outer edge;
   a facepiece is engaged to the outer edge of the base structure and surrounds the base structure;
   a side passageway is disposed on a side of the base structure and is surrounded by a rim on the external surface of the base structure that extends outwardly from the external surface, the rim including a first rim end engaged to the base structure, a second rim end distal to the base structure, and a key proximal the second rim end and offset from the first rim end, the key protruding radially outward from an annular body of the rim, the annular body adapted for oxygen to flow therethrough; and
   a hose attachment ring selectively secured to the rim, the hose attachment ring including a first concentric ring, a second concentric ring, and a follow tube, the first concentric ring including a shelf extending radially inward at an end of the first concentric ring, the shelf defining a juncture between the first concentric ring and the hollow tube, the second concentric ring extending from the first concentric ring in a direct opposite the hollow tube, the second concentric ring including a diameter smaller than that of the first concentric ring, and the second concentric ring is adapted to receive the rim therein,
   wherein the hose attachment ring includes a lip and a ridge, the lip extending radially inward from an end of the second concentric ring distal to the first concentric ring, the lip forming a keyed opening sized to receive the key, and the ridge extending radially inward at a position axially offset from the lip and circumferentially aligned with the keyed opening.

2. The breathing apparatus according to claim 1, wherein the rim includes a plurality of keys including the key, the plurality of keys being proximal the second rim end and offset from the first rim end and circumferentially spaced an equal distance apart.

3. The breathing apparatus according to claim 1, further comprising at least one front passageway disposed on the breathing apparatus.

4. The breathing apparatus according to claim 3, wherein the front passageway is adapted for oxygen to flow therethrough, the front passageway including a tube with a bend offset from the base structure, the tube extending to an outlet portion.

5. The breathing apparatus according to claim 4, wherein the outlet portion contains ridges on the external surface.

6. The breathing apparatus according to claim 3, wherein a plurality of front passageways are disposed on the breathing apparatus.

7. A breathing system, comprising:
a breathing apparatus, comprising:
- a rigid base structure having a top portion, a bottom portion, an internal surface, and an external surface, wherein the top portion contains an arcuate section for covering a user's nose and the bottom portion is wider than the top portion for covering a user's mouth, the base structure contains an outer edge;
- a facepiece is engaged to the outer edge of the base structure and surrounds the base structure;
- two side passageways, each being disposed on opposing sides of the base structure and each being surrounded by a rim on the external surface of the base structure that extends outwardly from the external surface; and
- two hose attachment rings, each being selectively secured to one of the rims;

a storage device;
two flexible hoses separately connected to the storage device, each connecting to one of the two hose attachment rings, such that the two flexible hoses connect to the breathing apparatus on the opposing sides of the base structure; and
an oxygen supply,
wherein each of the two hose attachment rings includes a first concentric ring, a second concentric ring, and a hollow tube, a first concentric ring including a shelf extending radially inward at an end of the first concentric ring, the shelf defining a juncture between the first concentric ring and the hollow tube, the second concentric ring extending from the first concentric ring in a direction opposite the hollow tube, the second concentric ring including a diameter smaller than that of the first concentric ring, and the second concentric ring is adapted to receive a corresponding rim therein, and wherein the corresponding rim includes a key protruding radially outward form an end of the corresponding rim distal to and offset from the rigid base stricture, and each of the two hose attachment rings including a lip and a ridge, the lip extending radially inward from an end of the second concentric ring distal to the first concentric ring, the lip forming a keyed opening sized to receive the key, and the ridge extending radially inward at a position axially offset from the lip and circumferentially aligned with the keyed opening.

8. The breathing system according to claim 7, wherein the storage device comprises
- a first side having an outer edge;
- a second side having an outer edge and the outer edge of the first side and the outer edge of the second side are engaged together forming an interior cavity;
- an inlet opening within either the first side or the second side for allowing oxygen to be inserted into the cavity;
- a plurality of outlet openings within the first side and/or second side for allowing oxygen to exit the storage device, each of the two flexible hoses connecting to separate outlet openings.

9. The breathing system according to claim 7, wherein each of the two flexible hoses includes a first end and a second end, wherein the first end is engaged to a first adaptor and the second end is engaged to a second adaptor, the first adaptor is engaged to a corresponding rim of the breathing apparatus and the second adaptor is engaged to a corresponding outlet in the storage device.

10. The breathing system according to claim 8, further comprising a hose having a first end and a second end, the first end of the hose engaged to the oxygen supply and the second end engaged to the inlet opening in the storage device.

11. The breathing system according to claim 7, wherein the storage device is composed of medical grade thermoplastic polyurethane.

* * * * *